United States Patent
Hetzel et al.

(10) Patent No.: US 9,511,197 B2
(45) Date of Patent: Dec. 6, 2016

(54) SURGICAL DEVICE FOR USE IN LAPAROSCOPY

(75) Inventors: Alexander Hetzel, Villingendorf (DE); Marc A. Reymond, Enger (DE); Tina Schwarz, Rottweil (DE)

(73) Assignees: Alexander Hetzel, Villingendorf (DE); Marc A. Reymond, Enger (DE)

( * ) Notice: Subject to any disclaimer, the term of this patent is extended or adjusted under 35 U.S.C. 154(b) by 24 days.

(21) Appl. No.: 14/122,338

(22) PCT Filed: May 29, 2012

(86) PCT No.: PCT/DE2012/100159
§ 371 (c)(1),
(2), (4) Date: Nov. 26, 2013

(87) PCT Pub. No.: WO2012/163346
PCT Pub. Date: Dec. 6, 2012

(65) Prior Publication Data
US 2014/0142495 A1    May 22, 2014

(30) Foreign Application Priority Data

May 27, 2011 (DE) .................... 20 2011 101 151 U

(51) Int. Cl.
*A61M 13/00* (2006.01)
*A61B 17/34* (2006.01)
(Continued)

(52) U.S. Cl.
CPC ........ *A61M 13/003* (2013.01); *A61B 17/3474* (2013.01); *A61M 13/00* (2013.01);604/24, 164.01; 606/41
See application file for complete search history.

(58) Field of Classification Search
CPC ............ A61B 17/3474; A61B 17/3494; A61B 17/00234; A61B 16/0093; A61M 13/00; A61M 13/003; A61M 15/02; A61M 11/02; A61M 2218/003; A61M 16/0093
(Continued)

(56) References Cited

U.S. PATENT DOCUMENTS 4,850,528 A * 7/1989 Hanus .......................... 229/138
5,139,478 A * 8/1992 Koninckx ........... A61M 13/003
600/560
(Continued)

FOREIGN PATENT DOCUMENTS

EP      2 248 470 A1   10/2010
GB      2 273 673 A    6/1994
(Continued)

OTHER PUBLICATIONS

International Search Report of PCT/DE2012/100159, mailed Oct. 26, 2012.

*Primary Examiner* — Theodore Stigell
(74) *Attorney, Agent, or Firm* — Slater Matsil, LLP

(57) ABSTRACT

A surgical device and a method for using the surgical device are disclosed. In an embodiment the device for applying a substance (X) in a hollow space of a body cavity such as a hollow organ, in particular a therapeutic pneumoperitoneum, includes a trocar system with a trocar sleeve, the trocar system having a gas connection to which an insufflation gas-supply line can be connected and a nozzle system, which in its interior forms a lumen with a proximal end and a distal end, wherein the nozzle system has a needle nozzle fixed at the distal end of the lumen, and wherein the nozzle system is guided by the trocar sleeve.

18 Claims, 2 Drawing Sheets

Figure 1:
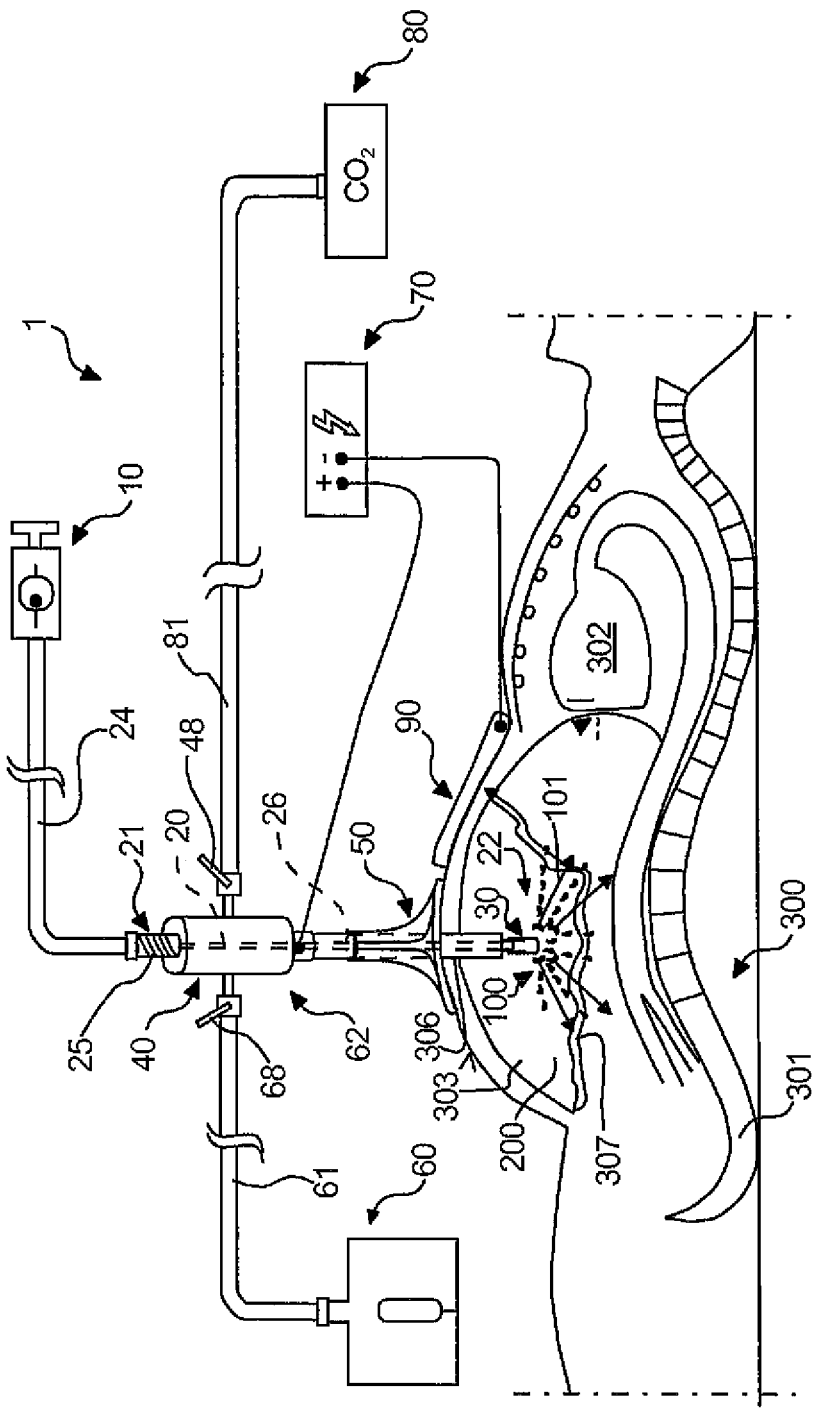

(51) Int. Cl.
*A61M 16/00* (2006.01)
*A61B 17/00* (2006.01)
*A61M 11/02* (2006.01)
*A61M 15/02* (2006.01)

(52) U.S. Cl.
CPC ... A61M 16/0093 (2014.02); *A61B 17/00234* (2013.01); *A61B 17/3494* (2013.01); *A61B 2218/003* (2013.01); *A61M 11/02* (2013.01); *A61M 15/02* (2013.01)

(56) References Cited

U.S. PATENT DOCUMENTS

| | | | |
|---|---|---|---|
| 5,429,636 A * | 7/1995 | Shikhman | A61B 17/3494 604/164.08 |
| 5,626,597 A | 5/1997 | Urban et al. | |
| 6,733,479 B1 | 5/2004 | Ott | |
| 2004/0030333 A1 | 2/2004 | Goble | |
| 2005/0113797 A1* | 5/2005 | Ott | A61M 13/003 604/506 |
| 2007/0088274 A1* | 4/2007 | Stubbs et al. | 604/164.01 |
| 2008/0082084 A1* | 4/2008 | Roberts | A61B 17/3474 604/540 |
| 2009/0088700 A1 | 4/2009 | Imbayashi | |
| 2010/0331766 A1* | 12/2010 | Hayakawa | A61B 17/00491 604/24 |

FOREIGN PATENT DOCUMENTS

| | | |
|---|---|---|
| WO | 2004/043274 A1 | 5/2004 |
| WO | 2008/030256 A1 | 3/2008 |

* cited by examiner

SURGICAL DEVICE FOR USE IN LAPAROSCOPY

CROSS REFERENCE TO RELATED APPLICATIONS

This application is the National Stage of PCT/DE2012/100159 filed on May 29, 2012, which claims priority under 35 U.S.C. §119 of German Application No. 20 2011 101 151.1 filed on May 27, 2011, the disclosure of which is incorporated by reference. The international application under PCT article 21(2) was not published in English.

The invention relates to a device for the directed application of a substance in a hollow space, such as a hollow organ, of a body cavity, in particular a therapeutic pneumoperitoneum.

From the general state of the art it is well known that in the treatment of diseases in the abdomen and thorax minimally invasive surgery can be performed by means of so-called keyhole surgery, also known as laparoscopy or thoracoscopy.

In order to perform keyhole surgery, a hollow space in the patient to be treated is needed. Typically, this hollow space is formed by a gas, preferably carbon dioxide $CO_2$ being introduced into the patient at a suitable point under a pressure of 12 to 15 mm Hg by means of a $CO_2$-insufflator. Access to the hollow space and for the surgical procedure is provided via operating trocars. Basically it can be said that surgical procedures are still mechanical and/or electrical interventions that do not incorporate other methods of treatment, such as medications, nano-molecules, etc.

According to the current state of the art during minimally invasive surgery the operating environment to be treated by this procedure is not treated in a controlled way. Only in exceptional cases a therapeutic rinsing with tumor-inhibitory or bactericidal substances is done.

The reason for this is that the therapeutic rinsing of the peritoneal cavity had been relatively ineffective. The peritoneum for example forms a barrier that is difficult to overcome. The rinsing solution thus often reaches only a small part of the peritoneal surface. Moreover, the diffusion of the therapeutic solution into the tissue is minimal. The same applies to the thorax and the pleura.

Thus, it is an object of the present invention to provide a simplified device for the directed introduction of a substance into a hollow space.

These objects are solved with the features of the independent claims. Further exemplary embodiments are specified in the claims which refer back to said claims.

Accordingly, a device is provided for the directed application of a substance in a hollow space, such as a hollow organ, of a body cavity, in particular a therapeutic pneumoperitoneum, comprising:
  a trocar system with a trocar sleeve, said trocar system having a gas connection to which an insufflation gas-supply line can be connected, and
  a nozzle system, which in its interior forms a lumen, with a proximal end and a distal end, wherein the nozzle system has a needle nozzle fixed at the distal end with the lumen and is guided by the trocar sleeve.

An idea of the invention is to provide a therapeutic device for therapeutically generating a pneumoperitoneum which allows the administration of substances, including medications and nano-molecules, in the form of an electrostatically charged aerosol during a surgical procedure in which the device according to the invention is applied.

This provides the advantage that the at least one substance achieves a better biological effect than the conventional rinsing because the substance is electrostatically charged during application. If the patient is grounded such as by a neutral electrode, an electrical gradient forms which enables better distribution of wetting of the substance in the operational environment of the pneumoperitoneum.

The hollow space may be the natural cavity of a hollow organ, such as the cavity of the heart, blood vessels, bile duct, urinary tract, gastrointestinal tract, uterus or brain ventricles. However, the term hollow space also comprises so-called body cavities, wherein a body cavity may comprise each hollow space in the body that is lined by mesothelium and epithelium, self-contained or connected with other cavities or the outside world such as the abdomen, thoracic cavity, cranial cavity, nasal cavity, oral cavity, pharynx, subarachnoid spaces, or joint cavities.

The nozzle system has no additional passage for surgical instruments arranged inside coaxially to the needle nozzle. This simplifies the construction of the nozzle system considerably. The needle nozzle can be configured as a needle valve.

In one embodiment of the device, an electrostatic charging section for electrostatically charging the aerosol is provided.

The aerosol has medically active nanoparticles. The adhesion to and penetration of tissue by nanoparticles is improved by means the electrostatic charge on the aerosol.

In one embodiment, on the trocar system a discharge port is formed with to which a discharge line is connectable.

By opening the shut-off valve at the discharge port, the insufflation gas can be selectively discharged after the surgery.

In a further embodiment a pump, in particular a micropump, for transporting the pressurized substance into the nozzle system is connectable to the nozzle system, such that the substance is convertible into the aerosol by means of a needle nozzle or a needle valve.

In a further embodiment the electrostatic charging section is electrically connectable to a first pole of a generator via an electric line in order to electrostatically charge the aerosol by means of the electric charge generated by the generator.

By use of the generator, the electrostatic charging can be done selectively.

In one embodiment, the generator has a second pole, which is connectable via a second electric line to a flat adhesive electrode.

The patient can be grounded with the adhesive electrode, and an electrical connection area is provided, which has a relatively large surface. Thereby, heating of the adhesive electrode and the skin, on which it rests, can be avoided.

According to one embodiment of the device according to the invention it is provided that a protective collar can be mounted to the trocar sleeve in a fluid-tight manner, the protective collar having a rosette portion for fluid tight fit on the trocar sleeve and a flat attachment portion adjacent to the rosette portion for fluid-tight attachment to a skin surface of a patient.

An advantage of the protective sleeve is an improved operational safety, so that for example the risk of contamination of the surgical environment, i.e. the exposure of personnel to dangerous substances can be limited or completely prevented.

According to one embodiment of the device according to the invention it is provided that the rosette portion of the protective collar is removably mountable to the trocar in a fluid-tight manner.

According to one embodiment of the device according to the invention it is provided that the attachment portion is formed of an elastic material and is, on the side intended for attachment to the patient, particularly the abdominal wall, provided with an adhesive agent configured to form a fluid-tight connection with the patient's skin.

According to one embodiment an insufflator is connectable to the trocar system, said insufflator providing the insufflation gas for forming a hollow space, in particular a therapeutic pneumoperitoneum, in a patient at 12 to 15 mm Hg.

The device can be used in a method for the directed application of a substance in a hollow space, such as a hollow organ, of a body cavity, in particular, a therapeutic pneumoperitoneum, with the steps:
a. inserting a trocar sleeve a trocar system with a trocar sleeve,
b. Supplying the trocar sleeve with an insufflation gas
c. Penetration of the trocar sleeve with a nozzle system, which in its interior forms a lumen, with a proximal end and a distal end, wherein the nozzle system has a needle nozzle fixed at the distal end with the lumen and is guided by the trocar sleeve,
d. Generating an aerosol in the hollow space via the needle nozzle.

According to one embodiment of the method, the needle nozzle is electrically connected to an electrostatic charging section.

According to one embodiment of the method according to the invention, mainly carbon dioxide is provided as insufflation gas.

Further advantageous embodiments of the invention and exemplary embodiments thereto will be explained in more detail below in conjunction with the accompanying drawings. Similarly functioning parts or components are partially provided with the same reference numerals. The terms "left", "right", "top", "bottom" used in the description of the embodiment refer to the drawing figures in alignment with human-readable names of the figures and references. For better understanding in the following figures the respective features are schematic and exaggerated and are not shown to scale.

In the drawing:

FIG. 1 shows a schematic overview of the device according to the invention for generating a therapeutic pneumoperitoneum in a patient, and FIG. 2 shows a view of the device according to the invention for generating a therapeutic pneumoperitoneum of FIG. 1.

FIG. 1 shows a schematic view of a device 1 according to the invention for producing a therapeutic hollow space 200, in particular a pneumoperitoneum in a patient 300. The patient may, as shown schematically in FIG. 1, be a human. The application of the device according to the invention, however, is not limited to humans but can be applied to other organisms. The term patient shall therefore describe organism being that requires medical treatment and can be treated with the apparatus according to the invention.

For better orientation, the spine 301, the heart 302 and an abdominal cavity 303 are indicated in the patient 300. The abdominal cavity 303 is formed as a hollow space 200 for a laparoscopic procedure and is exaggerated for better understanding. The hollow space is preferably made accessible through a minimally invasive surgical procedure (keyhole surgery) and is formed by the introduction of $CO_2$ into the abdominal cavity. For this purpose, the trocar system 40 according to the invention may be used, which can therefore be connected to an insufflator 80. During the keyhole surgery the hollow space is conventionally prepared with carbon dioxide ($CO_2$) at a pressure of 12 to 15 mm Hg. The access for the surgical procedure is secured by a suitable trocar, such as the trocar system 40 according to the invention.

The device 1 according to the invention for producing a therapeutic cavity can be applied for example in minimally invasive procedures in the following body cavities and in the following treatments:

Abdominal cavity (abdomen): Peri- and postoperative pain treatment, destruction of tumor cells (gastric cancer, ovarian cancer, other cancers), destruction of bacteria (peritonitis), prevention and treatment of peritoneal carcinomatosis, prevention of adhesions. Chest (thorax): Peri- and postoperative pain treatment, destruction of tumor cells (lung cancer, pleural cancer, other cancers), destruction of bacteria (pleuritis), prevention and treatment of pleural carcinosis. Further applications can be found in endoscopic surgeries in a non-preformed space (eg in the retroperitoneum).

With the aid of the device 1 according to the invention, as mentioned above, a hollow space 200 can be formed, wherein additionally an aerosol 100 can be applied, in particular in a directed manner, in the operating environment of the pneumoperitoneum 200. Directed application in this case means in particular, that an electrostatically charged aerosol may follow the gradient 101 of an electrostatic field shown by arrows (see FIG. 2). For this purpose, a suitable generator 70 is electrically connected to the trocar system 40 on one side and to the patient 300 on the other side.

Through the use of electrostatically charged particles or aerosol 100 and the grounding of the patient's body, the adhesion of the aerosol 100 to the peritoneum 307 is improved. Furthermore, the penetration depth of the electrostatically charged aerosol in the tissue of the surgical environment can be substantially improved.

To generate the electrostatic field on the patient or in the surgical environment of the hollow space 200, an adhesive electrode 90 is attached to the skin surface of the abdomen of the patient 300 by a suitable adhesive means. The adhesive electrode 90 is also connected to a generator 70, so that the patient is grounded. To generate the electrostatic field, the generator 70 is also electrically connected to the trocar system 40. The trocar system 40 is preferably made of an electrically conductive material, preferably surgical steel.

Preferably, prior to introduction of the electrostatically charged material in aerosol form, the hollow space 200 is formed by introducing a suitable insufflation gas, such as $CO_2$, into the patient. This state is shown in FIG. 1, wherein for a better understanding the size of the hollow space 200 is shown exaggerated.

The device 1 according to the invention further comprises a micro-pump 10 for transporting the liquid substance X. The substance X may be a suitable liquid, which may include additional substances for various purposes such as cancer treatment, pain treatment, treatment of infection, and the prevention of adhesions. The micro-pump 10 can be formed in one embodiment by a syringe, not shown, having a piston and a cylinder, wherein the syringe can be loaded in a device, not shown, and wherein said device compresses the piston, thereby generating a fluid pressure.

As further seen in FIG. 1, the device 1 according to the invention has a nozzle system 20, to which the micro-pump 10 is connected. The micro-pump 10 and the nozzle system 20 are connected to each other in a fluid conductive manner, so that a substance X, which is transported in a pressurized manner by the micro-pump 10, is atomized to a mist-like aerosol 100 by needle nozzle 30. In addition, the aerosol is electrostatically charged by a voltage applied to the trocar system 40. The substance may include in particular drugs suitable for chemotherapy, such as cytostatics, such as doxorubicin, lisplatin or other chemotherapeutic agents.

The nozzle system 20 extends completely through a cavity in the trocar system 40 and at its one end portion has a needle nozzle 30 for dispensing the aerosol in the surgical environment of the pneumoperitoneum 200. The nozzle system 20 is formed to create an aerosol 100 from the substance X. The nozzle system 20 includes a proximal end 21 and a distal end 22. At the proximal end 21, which protrudes upward out of the trocar system 40, a tube 24 may be connected via a thread 25. The tube 24 is connected to a micro-pump 10 in a fluid conducting manner. The nozzle system 20 forms in its interior a tubular lumen 26. Attached to the lumen 26 at a distal end 22 is a needle nozzle 30 configured for example as a needle valve To form a fluid-tight, closed system, an access 306 in the abdominal wall of the patient 300 is closed by a protective collar 50, which on the one hand is mounted fluid-tightly on the skin surface around access 306 and on the other hand fits fluid-tightly to the peripheral surface of the trocar system 40 with the trocar sleeve 45.

Furthermore, a filter device 60 is connected to the trocar system 40 for taking up contaminated aerosol from the pneumoperitoneum of a patient 300. The filter device 60 may be connected to the trocar system 40 after a surgical procedure in a fluid conducting manner in order to receive insufflation gas and therein substance X from the cavity 200 without contaminating the operating room with the substance X.

With the fluid-tight sealing of the trocar sleeve 45 by the collar 50 and the filter device 60, a closed circuit can be provided, whereby a contamination of the operating room and the operating personnel with contaminated aerosol is prevented during the surgical procedure, which contributes in addition to the operational safety.

Figure 2:
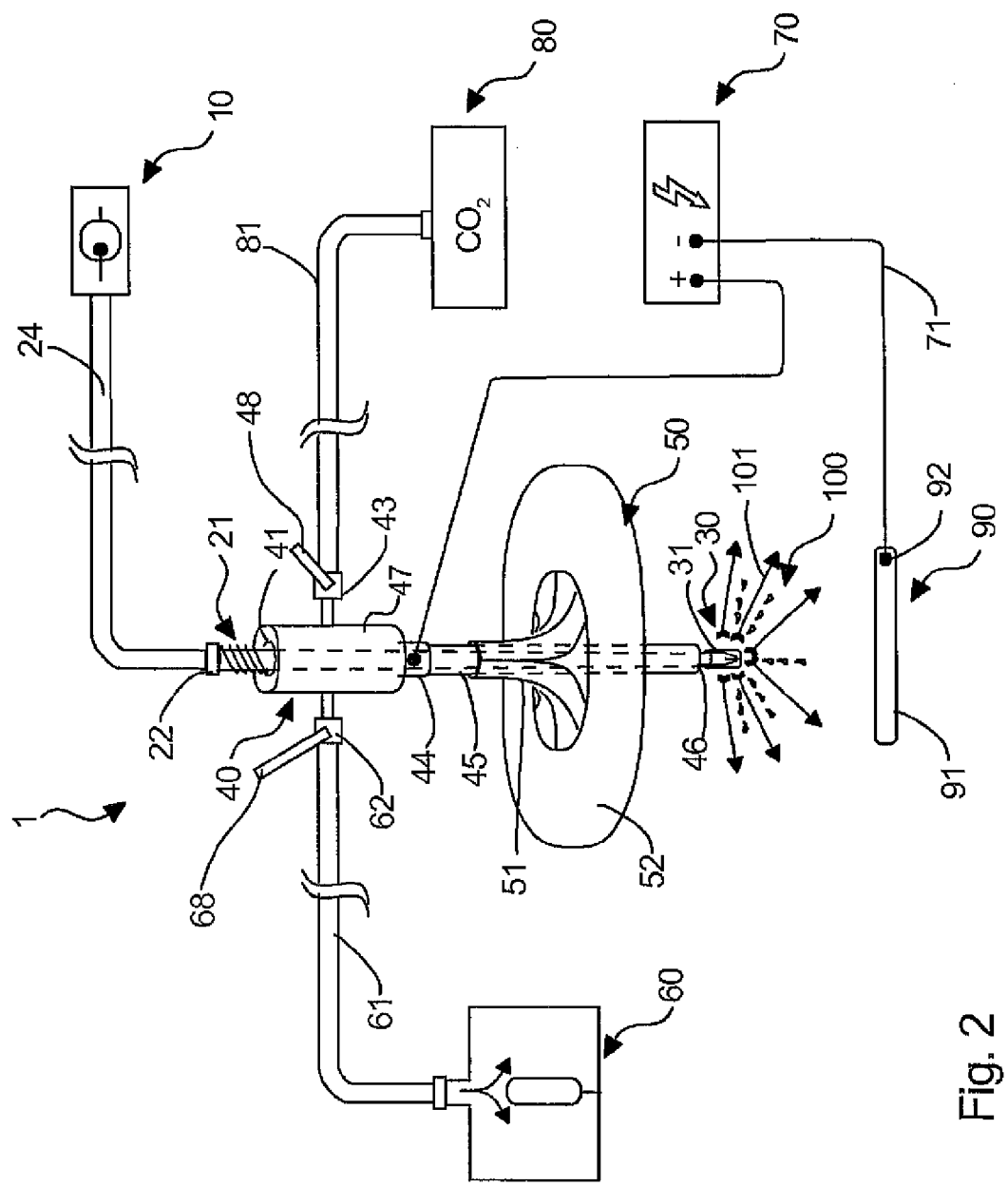

In FIG. 2, the individual components of the device 1 according to the invention are shown again in detail. The device 1 comprises thereafter a trocar system 40, a nozzle system 20 having a needle nozzle 30, a micro pump 10 connected to the nozzle system 20, a $CO_2$-insufflator 80, which is connected via an insufflation gas supply line 81 to the trocar system 40, a Filter device 60, which is connected to the trocar system 40, an electric generator 70 electrically connected to the nozzle system 20, an adhesive electrode 90 for grounding a patient 300, which is electrically connected to the generator 70, a protective collar 50 that is fluid-tightly mountable to a trocar sleeve 45 of the trocar system 40, and a filter device 60, which is connected to the trocar system 40.

The trocar system 40 has a connection portion 47 for connection of the insufflator 80 and for connecting the filter apparatus 60. For this purpose at the trocar system 40 a gas connection 43, which is lockable via a check valve 48 and to which a gas supply line 81 of the insufflator 80 is connected, and a closable discharge port 62 for connecting a discharge line 61, which is connected to the filter device 60, are formed. Further, the trocar system 40 has a trocar sleeve 45 that is insertable into a patient 300, and which is formed for guiding a surgical instrument such as the nozzle system 20 according to the invention. To accommodate the nozzle system 20, suitable cavities are formed in the trocar system 40, wherein in particular suitable sealing means are provided at the access opening 41 of the trocar system 40, which sealing means may fluid-tightly seal the nozzle system 20 at least at the access opening 41.

Further, the trocar system 40 has at the opposite end of the access opening 41 of the trocar sleeve 45 an exit port 46, through which the needle nozzle 30 of the nozzle system 20 is movable. Additionally, the device 1 has an electric generator 70 for the electrostatic charging of an aerosol. The generator 70 is electrically connected to the nozzle system 20. Thereby, the aerosol produced by the nozzle system 20, in particular the substance X, is electrostatically charged, so that the individual aerosol droplets can move according to the gradient 101 of an electrostatic field.

Further, an adhesive electrode 90 is provided on the generator 70 for grounding the patient. The adhesive electrode 90 has an attachment side 91, on which a suitable adhesive layer is preferably applied, so that an electrical connection between the adhesive electrode and the patient can be formed. The adhesive electrode 90 is electrically connected via an electrical port 92 via an electrical line 71 to the grounding of the generator 70.

If the adhesive electrode 90 and the trocar sleeve 45 are attached in a suitable manner to the patient and, by means of the generator 70, a voltage is applied between the adhesive electrode 90 and the nozzle system 20, an electrostatic field with a predetermined gradient may be generated, and the electrostatically charged aerosol 100 can distribute in the patient. It is hereby achieved that the electrostatically charged aerosol 100 and/or the substance X contained in the aerosol can penetrate in a directed manner into the surrounding tissue in the direction predetermined by the gradient 101.

To the gas port 43 of the trocar system 40 the insufflator 80 is connected via the gas supply line 81. The insufflator 80 generates the hollow space required for laparoscopy or thoracoscopy in a patient 300, wherein in the device 1 according to the invention, the insufflation gas can also be used in the nozzle system 20 to generate the aerosol.

To the discharge port 62 of the trocar system 40 a discharge line 61 is connected in a fluid-tight manner, which is also connected in a fluid-tight manner to a filter device 60 with a suitable filter via a filter device connection. Thus, a closed circuit of insufflation gas and contaminated aerosol from the hollow space of the patient is created to prevent contamination of the operating room and the operating personnel.

In order to close the access opening 306 in the patient in a fluid-tight manner a protective collar 50 is mounted on the trocar sleeve 45. The protective collar 50 has a rosette portion 51 for fluid-tight mounting to the trocar sleeve 45, and a flat attachment portion 52 adjacent to the rosette portion for fluid-tight attachment to a skin surface of a patient.

Preferably, the protective collar 50 is at least partially made of an elastic material so as to ensure a movement of the trocar system 40 while at the same time closing the access to the patient 306 in a sufficiently fluid-tight manner. On the side of the attachment portion 52, which is provided for attachment to the patient 300, particularly the abdomen, a suitable adhesive means is provided which can provide a fluid tight connection with the patient's skin and the attachment portion.

The invention claimed is:
1. A device for applying a substance (X) in a hollow space of a body cavity, the device comprising:
 a trocar system with a trocar sleeve, wherein the trocar system comprises a gas connection to which an insufflation gas-supply line is connectable, the trocar system configured to apply an insufflation gas into a body cavity thereby forming the hollow space;

a nozzle system, which in its interior forms a lumen, with a proximal end and a distal end, wherein the nozzle system has a needle nozzle fixed at the distal end of the lumen and is guided by the trocar sleeve, and wherein the nozzle system is configured to apply the substance (X) as an aerosol in the hollow space; and a filter device connectable to the trocar system in a fluid conducting manner, wherein the filter device is configured to receive and filter the insufflation gas and the contaminated aerosol from the hollow space.

2. The device according to claim 1, further comprising an electrostatic charging section for the electrostatic charging of the aerosol is disposed at the nozzle system.

3. The device according to claim 2, wherein the electrostatic charging section is electrically connectable to a first pole of a generator via an electric line in order to electrostatically charge the aerosol by an electric charge generated by the generator.

4. The device according to claim 3, wherein the generator has a second pole, which is connectable via a second electrical line to a flat adhesive electrode.

5. The device according to claim 1, wherein the trocar system comprises a discharge port to which a discharge line connected to the filter device is connectable.

6. The device according to claim 1, further comprising a pump for transporting the pressurized substance (X) into the nozzle system, wherein the pump is connectable to the nozzle system such that the substance (X) is convertible into the aerosol by the needle nozzle.

7. The device according to claim 1, further comprising a protective collar mountable to the trocar sleeve in a fluid-tight manner, the protective collar having a rosette portion for fluid-tight fit on the trocar sleeve and a flat attachment portion adjacent to the rosette portion for fluid-tight attachment to a skin surface of a patient.

8. The device according to claim 7, wherein the rosette portion of the protective collar is releasably mountable to the trocar sleeve in a fluid-tight manner.

9. The device according to claim 7, wherein the attachment portion comprises an elastic material and is, on a side intended for attachment to the patient, provided with an adhesive agent configured to form a fluid-tight connection with the skin surface of the patient.

10. The device according to claim 9, wherein an insufflator is connectable to the trocar system, the insufflator providing the insufflation gas for forming the hollow space in a patient at 12 to 15 mm Hg.

11. The device according to claim 1, wherein the hollow space is a therapeutic pneumoperitoneum.

12. A method for applying a substance (X) in form of an aerosol in a hollow space of a body cavity, the method comprising:

inserting a trocar sleeve of a trocar system into the body cavity;

supplying the trocar sleeve with an insufflation gas forming the hollow space;

penetrating the trocar sleeve with a nozzle system which in its interior forms a lumen, with a proximal end and a distal end, wherein the nozzle system has a needle nozzle fixed at the distal end with the lumen and is guided by the trocar sleeve;

supplying the aerosol to the hollow space via the needle nozzle; and receiving and filtering the insufflation gas and the contaminated aerosol with a filter device in a fluid conducting manner.

13. The method according to claim 12, wherein the needle nozzle is electrically connected to an electrostatic charging section.

14. The method according to claim 12, further comprising electrostatically charging aerosol particles so that the charged particles follow a gradient of an electrostatic field and penetrate a tissue of the hollow space.

15. The method according to claim 12, wherein the hollow space is a therapeutic pneumoperitoneum.

16. The method according to claim 12, further comprising generating an electrostatic field between the nozzle system and a patient so that aerosol particles are charged.

17. The method according to claim 12, wherein the hollow space is formed by introducing an insufflation gas before supplying the aerosol to the hollow space.

18. The method according to claim 12, wherein supplying the aerosol to the hollow space via the needle nozzle comprises pumping the substance (X) as the aerosol into the hollow space.

* * * * *